United States Patent [19]

Mathur et al.

[11] 3,937,810

[45] Feb. 10, 1976

[54] SKIN LIGHTENING COMPOSITION AND METHOD OF USING THE SAME

[75] Inventors: Girish Prasad Mathur; Kuruvakkat Kochu Govind Menon; Srinivasan Varadarajan, all of Bombay, India

[73] Assignee: Lever Brothers Company, New York, N.Y.

[22] Filed: June 12, 1974

[21] Appl. No.: 478,477

Related U.S. Application Data

[63] Continuation of Ser. No. 322,251, Jan. 9, 1972, Pat. No. 3,861,689.

[30] Foreign Application Priority Data

Jan. 11, 1972   United Kingdom................. 1236/72

[52] U.S. Cl. ...................... 424/62; 424/47; 424/59
[51] Int. Cl.² ........................................ A61K 7/135
[58] Field of Search ............................... 424/59, 62

[56] References Cited
UNITED STATES PATENTS

| | | | |
|---|---|---|---|
| 2,260,173 | 1/1941 | Dohrn et al........................ | 424/60 X |
| 2,377,188 | 5/1945 | Schwenk et al...................... | 424/59 |
| 2,628,184 | 2/1953 | Widmann........................... | 424/263 |
| 3,002,992 | 10/1961 | Wood.............................. | 424/60 X |
| 3,123,647 | 3/1964 | Duennenberger et al........ | 424/59 X |

FOREIGN PATENTS OR APPLICATIONS

1,224,145   3/1971   United Kingdom................... 424/62

OTHER PUBLICATIONS

Abelson et al., Biochemical Journal, 1965, Vol. 96, pp. 840–852 (pp. 861 relied on).
Biochemical Journal, 1963, Vol. 89.
Daniels et al., Journ. of Investigative Dermatology, 1960, Vol. 35, pp. 329 to 332.
Chem. Abstracts, 1959, Vol. 53, p. 15484.

*Primary Examiner*—Albert T. Meyers
*Assistant Examiner*—Dale R. Ore
*Attorney, Agent, or Firm*—Arnold Grant, Esq.

[57] ABSTRACT

Skin can be lightened by application of a composition containing a skin lightening amount of niacin and a physiologically acceptable carrier. Such a composition contains from 0.2% to about 10% by weight of niacin and optionally also a compound which absorbs ultraviolet light in the range 290–360 nm to counteract the tanning and burning effect of sunlight.

4 Claims, No Drawings

SKIN LIGHTENING COMPOSITION AND METHOD OF USING THE SAME

This is a continuation, of application Ser. No. 322,251, filed Jan. 9, 1972. Now U.S. Pat. No. 3,861,689.

This invention relates to skin cosmetic preparations which have a lightening effect on the skin.

Hitherto, skin preparations have been concerned with maintaining the colour of the skin against exposure to ultra-violet light and have been based upon materials which deflect and scatter incident ultra-violet light of the wavelength which produces the burning and tanning, or which absorb this light.

The colour of normal human skin is due to the presence of melanin, haemoglobin and carotenoids. Of these pigments, melanin is of prime importance in considerations of skin pigmentation and cosmetology. Melanin is synthesised by melanocytes, specialised cells of the basal layer of epidermis characterised by the presence of tyrosinase; this enzyme is responsible for the aerobic oxidation of 1-tyrosine to dopa and to dopa quinone, which in turn is converted to indole-5, 6-quinone. This monomer is then oxidised and polymerised to form a large polymer melanin which is believed to be attached, through its quinone linkages, to the amino or sulphydryl groups of the protein matrix of the pigment granules. Melanin is found in the form of fine dark-brownish granules. In highly pigmented skin the granules may also be present in the more deeply situated layers. The melanocytes in the skin of Negroes are similar to those in white races though generally more dendritic and larger. In skin of white races the melanocytes have a restricted production of small but fully melanized granules; in melanocytes of albinos, numerous granules are formed but they do not become melanized. It is believed that all melanocytes are capable of forming melanin, but except in very dark skins, only a proportion of those are engaged in this process. Thus, it is generally believed that the number of melanocytes in the skin does not vary substantially from individual to individual, only the melanin density and the distribution within the melanocytes varies widely amongst individuals.

Pigmentation of skin involves formation of melanin granules by melanocytes and their dispersion into the epidermis. While the melanocytes are sole producers of melanin the malpighian cell is the vehicle of melanin distribution or dispersion.

There has now been found a compound which lightens the skin, by, it is believed, retarding the melanin dispersion.

Accordingly, the present invention provides a skin lightening composition comprising up to 10% by weight of niacin in a cosmetically and a physiologically acceptable carrier.

It is believed that niacin reduces the effective concentration of cyclic adenylic acid (cyclic 3'-5'-AMP) which is thought to act as the second messenger mediating the action of various hormones including the melanocyte stimulating hormone involved in the dispersion of melanin. Cyclic 3' - 5'-AMP phosphodiesterase is an enzyme which degrades cyclic 3'-5'-AMP to adenosine-5'-monophosphate. The activity of this enzyme has now been shown to be stimulated by niacin. Thus niacin is believed to reduce the effective concentration of cyclic 3'-5'-AMP and hence the dispersion of melanin granules.

Niacin is, of course, known by other names, viz, nicotinic acid or pyridine β-carboxylic acid, and has been used in dietary treatments. It may be included in the skin cosmetic preparations of the invention in amounts from 0.1 to 10%, preferably 0.5–3% by weight of composition.

Suitable carriers are the conventional formulations in the cream, lotion, ointment and aerosol art.

Sunburn, melanogenesis, and pigmentation of skin are closely associated responses to irradiation by the erythemogenic spectrum. The photobiological changes that cause erythema also lead to melanogenesis and increased pigmentation. The so-called erythemogenic spectrum is generally considered to include wavelengths between 290 and 320 nm, with peaks at 297 or 300 – 307 nm. Light of wavelengths greater than 320 nm is not thought to produce erythema.

The increase of melanin pigment that follows exposure of skin to solar radiation or ultra-violet light from artificial sources involves two distinct photobiological processes:
  i. immediate pigment darkening of preformed pigment without induction of erythema, and
  ii. the primary melanization involving induction of erythema, formation of new pigment and its dispersion.

The wavelengths which lie in the range of 320–420 nm with a broad maxima at 420 nm are responsible for the immediate pigment darkening in skin of preformed pigment without induction of erythema. Primary melanisation is most effectively initiated by wavelengths shorter than 320 nm.

We have discovered a skin lightening composition which also imparts protection from the immediate pigment darkening and the primary melanization due to exposure to solar radiation.

Accordingly, in a second aspect the present invention provides a skin lightening composition comprising up to 10% by weight of niacin and an ultra-violet absorber absorbing in the range of 290 – 320 nm, preferably urocanic acid and/or a compound of the formula

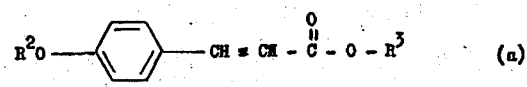

(a)

wherein $R^2$ is alkyl containing from 1 to 4 carbon atoms, preferably $CH_3$, and $R^3$ can be alkyl containing from 4 to 10 carbon atoms, preferably $C_6H_{13}$ or an alkoxyalkyl group of the type $-R^4-O-R^5$, wherein $R^4$ is alkylene containing from 1 to 4 carbon atoms and $R^5$ is alkyl containing from 1 to 4 carbon atoms.

To endow the compositions with tanning prevention properties, a compound having maximum absorption in the tanning ray region of the spectrum, viz, 320 – 360 nm may be used. Examples of such compounds have the general formula

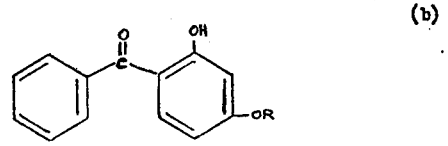

(b)

wherein R is alkyl containing from 4 to 12 carbon atoms, preferably $C_8H_{17}$.

These general classes of ultra-violet absorber will now be referred to as "u.v. absorbers (a) "and" (b)" respectively.

Of the foregoing examples, the preferred U.V. absorbers are selected from urocanic acid alone, and Givtan F (commercially available from Givaudin). For compositions having tanning prevention properties also, Cyasorb 531 (commercially available from the American Cyanamid Company) is the preferred U.V. absorber (b) to be used in association with niacin and a U.V. absorber (a).

The advantages of using niacin in association with a U.V. absorber in each of the ranges 290–320 nm and 320–360 nm, is that the resultant skin preparation not only lightens the skin, but protects it from both burning rays and tanning rays.

Appropriate amounts of U.V. absorbers (a) are from 0.1 to 4% by weight of composition and of U.V. absorber (b) 0.1 to 4% by weight of composition, and when urocanic acid is used, the latter may be present in 0.1 to 10% by weight of the composition.

The present invention will be further described by way of the following examples of cosmetic creams:

|  | Example 1 % by weight | Example 2 % by weight | Example 3 % by weight | Example 4 % by weight | Example 5 % by weight | Example 6 % by weight | Example 7 % by weight |
|---|---|---|---|---|---|---|---|
| Mineral oil | 3.00 | — | 3.00 | 3.00 | 3.00 | 3.00 | 3.00 |
| Glycerol monostearate | 3.00 | — | 3.00 | 3.00 | 3.00 | 3.00 | 3.00 |
| Nipagin | 0.10 | 0.05 | 0.10 | 0.10 | 0.10 | 0.10 | 0.10 |
| Stearic acid | 10.00 | 24.00 | 10.00 | 10.00 | 10.00 | 10.00 | 10.00 |
| Disodium orthophosphate | 0.70 | — | 0.70 | 0.70 | 0.70 | 0.70 | 0.70 |
| Citric Acid | 0.04 | — | 0.04 | 0.04 | 0.04 | 0.04 | 0.04 |
| Sodium Hydroxide | 0.46 | 0.20 | 0.46 | 0.46 | 0.46 | 0.46 | 0.46 |
| Triethanolamine | — | 1.00 | — | — | — | — | — |
| Urocanic Acid | 0.50 | 0.05 | 0.05 | — | — | 2.00 | — |
| Niacin | 1.00 | 1.00 | 1.00 | 3.00 | 2.00 | 1.00 | 10.00 |
| Givtan F | — | 2.00 | 2.00 | — | 2.00 | 2.00 | — |
| CyasorbUV531 | — | 2.00 | 2.00 | — | — | — | — |
| Polyethylene glycol | 5.00 | — | 5.00 | 5.00 | 5.00 | 5.00 | 5.00 |
| Isopropylmyristate | — | 4.00 | — | — | — | — | — |
| Glycerol | — | 7.50 | — | — | — | — | — |
| Water to | 100 | 100 | 100 | 100 | 100 | 100 | 100 |

The skin lightening effect of the formulation of these inventions has been demonstrated in clinical testing in human subjects against a placebo formulation without any actives. The skin lightening effect is gradual and reversible - the colour of the skin returning to normal a few weeks after discontinuing use of this cream. The formulation based on the present invention provides a safe and gradual means of obtaining a fairer complexion.

What is claimed is:

1. A method of lightening the skin which comprises applying to the skin a composition containing a skin lightening amount of niacin of from 0.2 to about 10% by weight and a physiologically acceptable carrier for niacin.

2. A cosmetic composition for application to the skin comprising a skin lightening amount of niacin of from about 0.2 to about 10% by weight, from 0.1 to 10% by weight of urocanic acid absorbing in the range of 290–320 nm and a physiologically acceptable carrier for niacin.

3. A cosmetic composition for application to the skin comprising a skin lightening amount of niacin of from 0.2 to 10% by weight and from 0.1 to 4% by weight of an ultra-violet absorber absorbing in the range of 290–320 nm having the formula

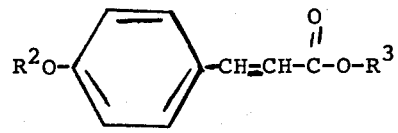

wherein $R^2$ is alkyl having 1–4 carbon atoms, $R^3$ is alkyl having 4–10 carbon atoms, or an alkoxyalkyl group of the formula $-R^4-O-R^5$, wherein $R^4$ is alkylene having 1–4 carbon atoms and $R^5$ is alkyl having 1–4 carbon atoms and a physiologically acceptable carrier for niacin.

4. A cosmetic composition for application to the skin comprising a skin lightening amount of niacin of from 0.2 to 10% by weight and from 0.1 to 4% by weight of an ultra-violet absorber absorbing in the range of 320–360 nm represented by the formula

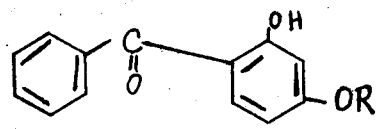

wherein R is an alkyl group containing from 4 to 12 carbon atoms and a physiologically acceptable carrier for niacin.

* * * * *